US00PP21051P2

(12) United States Plant Patent
Bradford

(10) Patent No.: US PP21,051 P2
(45) Date of Patent: Jun. 8, 2010

(54) INTERSPECIFIC TREE NAMED 'PLUMRED VI'

(50) Latin Name: ***Prunus* sp.**
Varietal Denomination: Plumred VI

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 0 days.

(21) Appl. No.: 12/319,516

(22) Filed: Jan. 9, 2009

(51) Int. Cl.
*A01H 5/00* (2006.01)

(52) U.S. Cl. ..... Plt./180

(58) Field of Classification Search ..... Plt./180
See application file for complete search history.

*Primary Examiner*—Kent L Bell

(57) ABSTRACT

The present invention relates to an interspecific tree and more particularly to a new and distinct variety broadly characterized by a medium size, moderately vigorous, hardy, and productive tree. Being self-unfruitful, the present variety requires cross pollination from an apricot, interspecific, or plum that blooms during the late season. The present variety produces a moderate bloom with an average amount of pollen to entice good bee activity to facilitate pollination. The fruit matures under the ecological conditions described during the last half of July, with first picking on Jul. 21, 2008. The fruit is uniformly large in size, full red in skin color, clingstone in type, globose in shape, full red in flesh color, firm in texture, and very good in flavor.

1 Drawing Sheet

Botanical classification: *Prunus* sp.
Varietal denomination: 'PLUMRED VI'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits. The present invention relates to a new and distinct variety of interspecific tree which has been denominated varietally as 'Plumred VI'.

During a typical blooming season I isolate as seed parents both individual and groups of different plum trees by covering them with screen houses. A hive of bees is placed inside each such house, and bouquets to provide pollen from different plum, apricot, and interspecific plum-apricot hybrid trees are placed in buckets near the trees approximately every two days for the duration of the bloom. During 2000 one tree of 'Fortune' (unpatented) plum was crossed by me in this manner. To pollinate this isolated tree, I selected bouquets from several sources of apricot and interspecific plum-apricot hybrid trees without keeping specific written details. Upon reaching maturity the fruit from this plum tree was harvested and the seeds were removed, cracked, stratified and germinated as a group with the label "H4". They were grown as seedlings on their own root in my greenhouse and upon reaching dormancy transplanted to a cultivated area of my experimental orchard located near Le Grand, Calif. in Merced County (San Joaquin Valley). During the spring of 2003 the claimed variety was selected by me as a single plant from the group of seedlings described above. Subsequent to origination of the present variety of interspecific tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was true to type.

The present variety is similar to its seed parent, 'Fortune' (unpatented) plum, by being self-unfruitful and by producing fruit that is similar in size, clingstone in type, and red in skin color, but is distinguished therefrom by producing fruit that is nearly full red in flesh color, that is globose in shape, that is much sweeter in flavor, and that matures about seven days later.

SUMMARY OF VARIETY

The present interspecific variety is characterized by a medium size, moderately vigorous, hardy, and productive tree. Being self-unfruitful, the present variety requires cross pollination from an apricot, interspecific, or plum that blooms during the late season. The present variety produces a moderate bloom with an average amount of pollen to entice good bee activity to facilitate pollination. The fruit matures under the ecological conditions described during the last half of July, with first picking on Jul. 21, 2008. The fruit is uniformly large in size, full red in skin color, clingstone in type, globose in shape, full red in flesh color, firm in texture, and very good in flavor.

DRAWING

The accompanying photograph consists of four whole fruits positioned to display the characteristics of the skin color and form, two half fruits divided to reveal the flesh and stone, a young tip shoot growth, typical leaves, and two insets depicting the flower buds and blossoms as they appeared on the tree during the blooming season.

DETAILED BOTANICAL DESCRIPTION

Referring now more specifically to the pomological characteristics of this new and distinct variety of interspecific tree, the following has been observed under the ecological conditions prevailing near Le Grand, Merced County (San Joaquin Valley), Calif. The fruit description was developed at the state of full ripe on Jul. 21, 2008, on the original tree during its eighth growing season. The flower and bud descriptions were developed during the previous blooming season. All major color code designations are by reference to the Inter-Society Color Council, National Bureau of Standards. Common color names are also used occasionally.

Parentage

Seed parent: 'Fortune' plum (unpatented).
Pollen parent: Unknown.

Tree

Size: Medium, reaching a height of 12' [3.66 m.] and a spread of 9' [2.74 m.] after eight growing seasons utilizing typical dormant pruning.

Vigor: Moderately vigorous, responding typically to irrigation and fertilization. The variety grows about 4' [1.22 m.] of surplus top-growth during the spring and summer. The plant should be grown on a standard commercial rootstock for production purposes.

Growth: Spreading and open.

Form: Pruned to a vase form.

Hardiness: Half hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Very productive, thinning usually necessary.

Fertility: Self-unfruitful, requiring cross pollination by a suitable late seasonal blooming apricot, interspecific, or plum, such as 'Plumsweet IV' (U.S. Plant Pat. No. 16,461) interspecific tree.

Bearing: Regular bearer, with no crop failures observed.

Trunk:

*Size.*—Medium, reaching a maximum diameter of 4½" [114.3 mm.] after the eighth growing season.

*Texture.*—Medium shaggy.

*Bark color.*—Dark grayish yellowish brown [81. d.gy.yBr] with Moderate orange yellow [71. m.OY] crevices present.

*Lenticels.*—Approximate Number Per Square Inch: 5. Color: Moderate orange yellow [71. m.OY]. Average Size: ⅜" [9.5 mm.]. Shape: Elongated, eye-shaped.

Branches:

*Size.*—Diameter of the scaffold is 2⅜" [60.3 mm.] measured 12" above the crotch reducing to 1⅝" [41.3 mm.] measured 12" above the next fork.

*Texture.*—Smooth on first year wood, increasing roughness with age.

*Color.*—1st Year Wood Topside: Deep yellowish brown [75. deep yBr]. 1st Year Wood Underside: Strong yellow green (117. s.YG). 2nd Year Wood: Strong brown [55. s.Br] with Dark orange yellow [72. d.OY] crevices present.

*Lenticels.*—Number Per Square Inch: More than 60 on second year wood. Color: Light yellowish brown [76. l.yBr]. Average Size: 1/32" [0.8 min.]. Shape: Eye shaped.

Leaves:

*Size.*—Medium. Average Length: 3⅛" [79.4 mm.]. Average Width: 1 15/16" [49.2 mm.].

*Arrangement.*—Alternate.

*Thickness.*—Medium.

*Form.*—Elliptical.

*Apex.*—Acuminate.

*Base.*—Acute with an average angle base angle of 75 degrees.

*Surface.*—Smooth.

*Color.*—Dorsal Surface: Moderate olive green [125. m.OlG]. Ventral Surface: Moderate yellow green [120. m.YG].

*Margin.*—Finely serrate.

*Venation.*—Pinnately net veined.

*Petiole.*—Average Length: 7/16" [11.1 mm.]. Average Thickness: 1/16" [1.6 mm.]. Color: Brilliant yellow green [116. brill.YG], often Deep red [13. deep R] where exposed to direct sunlight.

*Stipules.*—Number: 2 per leaf at young stage, up to 6 per growing tip. Average Length: 7/16" [11.1 mm.]. Color: Light yellow green [119. l.YG] becoming Light reddish brown [42. l.rBr] with age.

*Glands.*—Number: Mostly 2 per leaf. Position: Alternately positioned at the intersection of the petiole and the leaf blade. Size: Small. Form: Globose. Color: Light yellow green [119. l.YG] becoming Moderate reddish brown [43. m.rBr] with age. Leaf buds: Pointed, medium.

Flower buds:

*Hardiness.*—Hardy, with respect to central California winters.

*Diameter.*—Typically 3/16" [4.8 mm.] 1 week before bloom.

*Length.*—Typically ⅜" [9.5 mm.] 1 week before bloom.

*Form.*—Not appressed.

*Surface.*—Pubescent.

*Tip color.*—White [263. White].

Flowers: Perfect, complete, perigynous, usually a single pistil, typically thirty or more stamens, five sepals and petal locations alternately positioned.

*Average flower diameter.*—1 1/16" [27.0 mm.].

*Number of petals.*—Five, no double blossoms observed.

*Petal shape.*—Oval to circular.

*Petal margin.*—Entire, slightly wavy.

*Average petal diameter.*—½" [12.7 mm.].

*Average petal length.*—9/16" [14.3 mm.].

*Petal apex.*—Rounded.

*Petal base.*—Obtuse.

*Petal color.*—White [263. White] on both sides.

*Anther color.*—Very yellow [82. v.Y].

*Stigma color.*—Light greenish yellow [101. l.gY].

*Sepal color.*—Strong yellow green [117. s.YG] on the outer surface.

*Sepal length.*—7/32" [5.6 mm.].

*Sepal width.*—5/32" [4.0 mm.].

*Sepal apex.*—Rounded to elliptical to match the width and length.

*Sepal margin.*—Fairly smooth to the naked eye, slightly serrated when magnified.

*Average pistil length.*—9/16" [14.3 mm.].

*Average stamen length.*—½" [12.7 mm.].

*Fragrance.*—Moderate.

*Pollen production.*—Moderate, average bee enticement.

*Blooming period.*—Late, six days after 'Santa Rosa' plum (unpatented).
*Onset of bloom.*—One percent on Mar. 1, 2008.
*Date of full bloom.*—Mar. 8, 2008.
*Duration of bloom.*—One to two weeks, dependent on ambient temperature.
*Bloom density.*—Moderate.
*Number per cluster.*—2 to 8, mostly 2.

FRUIT

Maturity when described: Full ripe, Aug. 3, 2008.
Date of first picking: Jul. 21, 2008.
Date of last picking: Aug. 5, 2008.
Size: Uniform, Large.
*Average diameter axially.*—2⅝" [66.7 mm.].
*Average diameter across cheek plane.*—2⅝" [66.7 mm.].
*Average diameter across suture plane.*—2⅝" [66.7 min.].
*Typical weight.*—6.6 ounces [187 grams].
Form: Globose, mostly symmetrical.
*Longitudinal section form.*—Round.
*Transverse section through diameter.*—Round.
Suture: An inconspicuous Light orange yellow [70. l.OY] line located in a very shallow trough extending from the base to just beyond the pistil point.
Ventral surface: Rounded, very slightly lipped toward base.
Lips: Slightly unequal.
Cavity: Flaring, slightly elongated in suture plane, suture showing on one side.
*Depth.*—½" [12.7 mm.].
*Breadth.*—1⅛" [28.6 mm.].
Base: Truncate, moderately cordate if viewed parallel to the suture.
Apex: Rounded to slightly truncate.
Pistil point: An inconspicuous Light brown [57. l.Br] dot.
Stem: Medium.
*Average length.*—7/16" [11.1 mm.].
*Average width.*—1/16" [1.6 mm.].
Skin:
*Thickness.*—Medium.
*Surface.*—Smooth.
*Tenacity.*—Tenacious to the flesh.
*Astringency.*—Slight.
*Tendency to crack.*—None observed in dry seasons.
*Color.*—Very dark red [17. v.d.R] over a Moderate red [15. m.R] background with Light yellowish brown [76. 1.yBr] freckling throughout.
*Bloom.*—Moderate.
Flesh:
*Color.*—Dark red [16. d.R] near skin smoothly blending to Dark pink [6. d.Pk] toward the stone with Dark red [16. d.R] veins throughout.
*Surface of pit cavity.*—Covered with Dark pink [6. d.Pk] broken fibers when twisted away from stone.
*Amygdalin.*—Moderate.
*Juice.*—Abundant, rich.
*Texture.*—Firm, tough, meaty.
*Fibers.*—Abundant, fine, tender.
*Ripens.*—Somewhat earliest at apex.
*Flavor.*—A tasty balance of acid and sugar, typically 20 brix.
*Aroma.*—Slight.
*Eating quality.*—Very good.

STONE

Type: Clingstone.
Form: Oval.
Hilum: Narrow, oblong.
Base: Rounded, slightly oblique.
Apex: Obtuse.
Sides: Equal.
Surface: Rough throughout with a groove on each side of the dorsal fin.
External color of stone: Dark reddish orange [38. d.rO] when first removed.
Pit wall color when cracked: Light brown [57. l.Br].
Cavity surface color: Light grayish yellowish brown [79. l.gy.yBr].
Average pit wall thickness.—1/16" [1.6 mm.]
Average width.—¾" [19.1 mm.].
Average length.—1 1/16" [27.0 mm.].
Average breadth.—⅜" [9.5 mm.].
Tendency to split: Slight.
Kernel:
*Form.*—Oval.
*Skin color.*—Pale yellow [89. p.Y] when first removed.
*Pellicle color.*—Grayish yellow [90. gy.Y].
*Vein color.*—Dark orange yellow [72. d.OY].
*Taste.*—Bitter.
*Viable.*—Yes.
*Average width.*—7/16" [11.1 mm.].
*Average length.*—⅝" [15.9 mm.].
*Amygdalin.*—Moderate.

Use

Market: Fresh market and long distance shipping.
Keeping quality: Good, fruit quality observed to remain in good condition after 30 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of interspecific tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of interspecific *Prunus* sp. tree, substantially as illustrated and described, that is similar to its seed parent, 'Fortune' (unpatented) plum, by being self-unfruitful and by producing fruit that is similar in size, clingstone in type, and red in skin color, but is distinguished therefrom by producing fruit that is nearly full red in flesh color, that is globose in shape, that is much sweeter in flavor, and that matures about seven days later.

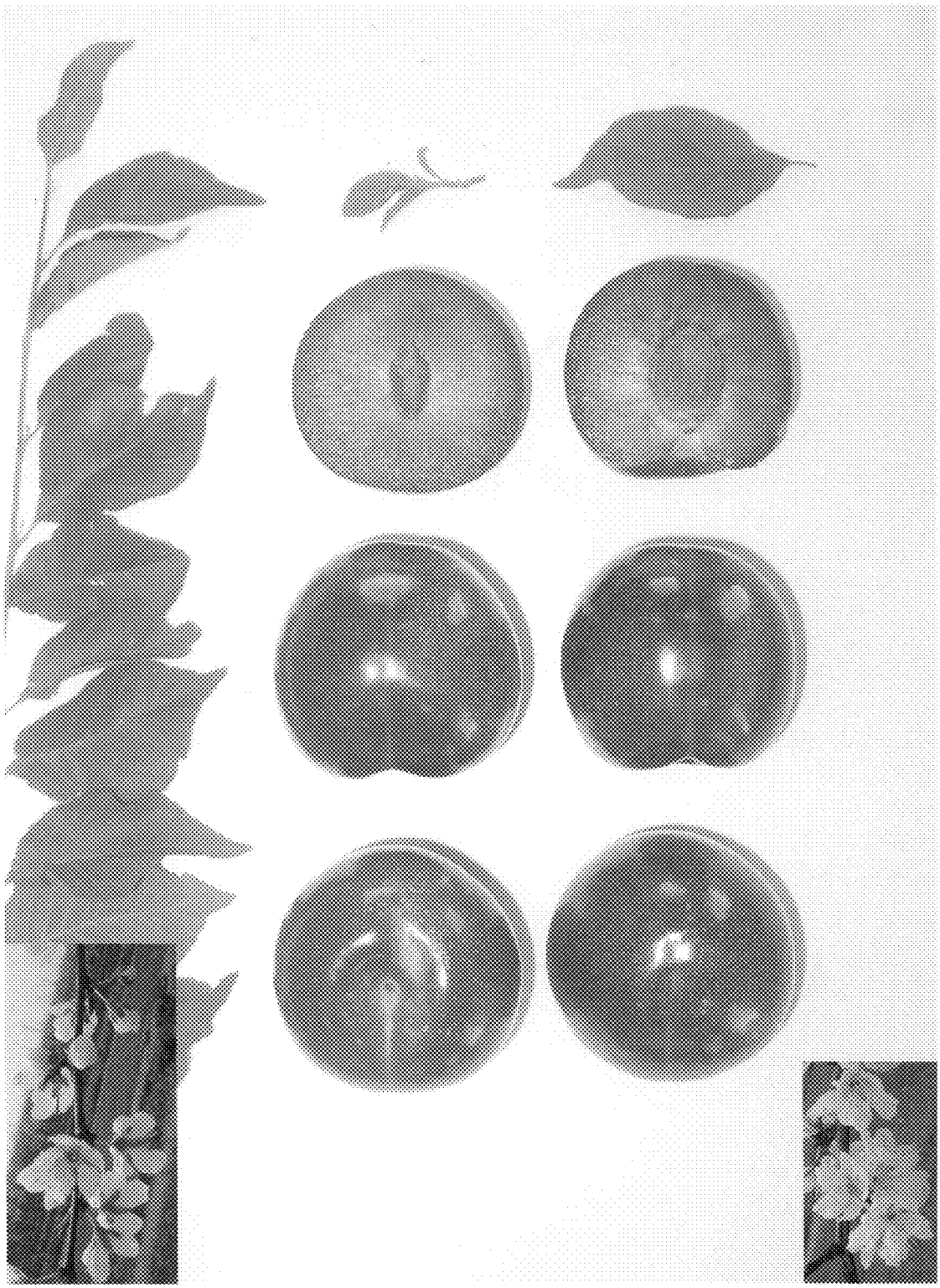

* * * * *